(12) United States Patent     (10) Patent No.: US 12,661,256 B2

Hale et al.     (45) Date of Patent: Jun. 23, 2026

(54) HEAT TRANSFER SYSTEM FOR A THERAPY DEVICE

(71) Applicant: Lear Corporation, Southfield, MI (US)

(72) Inventors: David Hale, Southfield, MI (US); Joshua Hallock, Warren, MI (US); Vyachislav Ivanov, West Bloomfield, MI (US); Samuel Blair, Troy, MI (US)

(73) Assignee: LEAR CORPORATION, Southfield, MI (US)

( * ) Notice: Subject to any disclaimer, the term of this patent is extended or adjusted under 35 U.S.C. 154(b) by 549 days.

(21) Appl. No.: 18/087,850

(22) Filed: Dec. 23, 2022

(65) Prior Publication Data

US 2024/0207088 A1    Jun. 27, 2024

(51) Int. Cl.
    *A61F 7/00*       (2006.01)
    *F25B 21/04*     (2006.01)

(52) U.S. Cl.
    CPC .......... *A61F 7/0085* (2013.01); *A61F 7/0053* (2013.01); *F25B 21/04* (2013.01); *A61F 2007/0075* (2013.01)

(58) Field of Classification Search
    CPC ............ A61F 2007/0075; A61F 7/0053; A61F 7/007; A61F 7/0085
    See application file for complete search history.

(56) References Cited

U.S. PATENT DOCUMENTS

| | | |
|---|---|---|
| RE30,491 E | 1/1981 | Gomez |
| 4,865,383 A | 9/1989 | Sbaragli et al. |
| 5,092,316 A | 3/1992 | Taylor et al. |
| 5,294,085 A | 3/1994 | Lloyd et al. |
| 5,551,755 A | 9/1996 | Lindberg |
| 5,658,046 A | 8/1997 | Rus |
| 5,658,050 A | 8/1997 | Lorbiecki |
| 5,711,575 A | 1/1998 | Hand et al. |
| 5,811,186 A | 9/1998 | Martin et al. |
| 5,971,478 A | 10/1999 | Hurite |
| 5,975,629 A | 11/1999 | Lorbiecki |
| 6,129,419 A | 10/2000 | Neale |

(Continued)

FOREIGN PATENT DOCUMENTS

| | | |
|---|---|---|
| CN | 109689428 A | 4/2019 |
| CN | 213322780 U | 6/2021 |

(Continued)

OTHER PUBLICATIONS

Barker, "BMW's Heated Seats as a Service Model Has Drivers Seeking Hacks", https://www.wired.com/story/bmw-heated-seats-as-a-service-model-has-drivers-seeking-hacks, Jul. 24, 2022, 13 pages.

(Continued)

*Primary Examiner* — Tigist S Demie

(74) *Attorney, Agent, or Firm* — Carlson, Gaskey & Olds, P.C.

(57) ABSTRACT

A system is provided with a thermoelectric device with a first heat transfer surface and a second heat transfer surface adapted for cooperation with a therapy device such that the first heat transfer surface is spaced apart from a contact surface of the therapy device to transfer heat to or from the contact surface. A fluid heat transfer system is in fluid communication with the thermoelectric device to transfer heat to or from the thermoelectric device.

22 Claims, 2 Drawing Sheets

(56) References Cited

U.S. PATENT DOCUMENTS

| | | | |
|---|---|---|---|
| 6,273,810 | B1 | 8/2001 | Rhodes, Jr. et al. |
| 6,869,140 | B2 | 3/2005 | White et al. |
| 6,893,086 | B2 | 5/2005 | Bajic et al. |
| 7,040,710 | B2 | 5/2006 | White et al. |
| 7,052,091 | B2 | 5/2006 | Bajic et al. |
| 7,197,801 | B2 | 4/2007 | Bajic et al. |
| 7,229,129 | B2 | 6/2007 | White et al. |
| 7,434,282 | B2 | 10/2008 | Fraser et al. |
| 7,478,869 | B2 | 1/2009 | Lazanja et al. |
| 7,637,573 | B2 | 12/2009 | Bajic et al. |
| 7,735,932 | B2 | 6/2010 | Lazanja et al. |
| 7,775,602 | B2 | 8/2010 | Lazanja et al. |
| 7,874,616 | B2 | 1/2011 | D'Agostini |
| 7,892,991 | B2 | 2/2011 | Yamanaka et al. |
| 7,946,649 | B2 | 5/2011 | Galbreath et al. |
| 7,971,931 | B2 | 7/2011 | Lazanja et al. |
| 8,038,222 | B2 | 10/2011 | Lein et al. |
| 8,162,391 | B2 | 4/2012 | Lazanja et al. |
| 8,162,398 | B2 | 4/2012 | Colja et al. |
| 8,360,517 | B2 | 1/2013 | Lazanja et al. |
| 8,662,583 | B2 | 3/2014 | Guadagno |
| 8,777,320 | B2 | 7/2014 | Stoll et al. |
| 8,814,267 | B2 | 8/2014 | Welch, Sr. et al. |
| 9,080,581 | B2 | 7/2015 | Bocsanyi et al. |
| 9,266,455 | B2 | 2/2016 | Uramichi et al. |
| 9,278,633 | B2 | 3/2016 | Brncick et al. |
| 9,440,567 | B2 | 9/2016 | Lazanja et al. |
| 9,561,744 | B2 | 2/2017 | Galbreath et al. |
| 9,615,670 | B2 | 4/2017 | Takaoka |
| 9,751,442 | B2 | 9/2017 | Smith |
| 9,862,244 | B2 | 1/2018 | Kim et al. |
| 9,938,649 | B2 | 4/2018 | Taninaka et al. |
| 9,945,490 | B2 | 4/2018 | Dankbaar et al. |
| 9,970,140 | B2 | 5/2018 | Taninaka et al. |
| 9,970,564 | B2 | 5/2018 | Dankbaar et al. |
| 10,065,543 | B2 | 9/2018 | Persson et al. |
| 10,107,410 | B2 | 10/2018 | Dankbaar et al. |
| 10,160,356 | B2 | 12/2018 | Ofy et al. |
| 10,207,619 | B2 | 2/2019 | Dankbaar et al. |
| 10,214,129 | B2 | 2/2019 | Jaranson et al. |
| 10,384,574 | B2 | 8/2019 | Fang |
| 10,414,303 | B2 | 9/2019 | Fujikake et al. |
| 10,625,643 | B2 | 4/2020 | Iacovone et al. |
| 10,676,000 | B2 | 6/2020 | Galbreath et al. |
| 10,696,202 | B2 | 6/2020 | Sedenka |
| 10,710,480 | B2 | 7/2020 | Iacovone et al. |
| 10,752,145 | B2 | 8/2020 | Steinberger et al. |
| 10,773,615 | B2 | 9/2020 | McElroy et al. |
| 10,786,162 | B2 | 9/2020 | Benson et al. |
| 10,793,041 | B2 | 10/2020 | Steinberger et al. |
| 10,856,664 | B2 | 12/2020 | Bhatia et al. |
| 10,899,262 | B2 | 1/2021 | Wheeler |
| 11,014,478 | B2 | 5/2021 | Benthaus et al. |
| 11,065,991 | B2 | 7/2021 | Iacovone et al. |
| 11,091,072 | B2 | 8/2021 | Greenwood et al. |
| 11,247,529 | B2 | 2/2022 | Zhou et al. |
| 2002/0096931 | A1 | 7/2002 | White et al. |
| 2003/0038517 | A1 | 2/2003 | Moran et al. |
| 2003/0075960 | A1 | 4/2003 | Wilkerson et al. |
| 2004/0004376 | A1 | 1/2004 | Cabebe |
| 2005/0066423 | A1 | 3/2005 | Hogan |
| 2006/0208540 | A1 | 9/2006 | Lofy et al. |
| 2006/0217644 | A1 | 9/2006 | Ozaki et al. |
| 2007/0035165 | A1 | 2/2007 | Zahel |
| 2010/0207443 | A1 | 8/2010 | Brncick |
| 2012/0299360 | A1 | 11/2012 | Welch, Sr. et al. |
| 2013/0097777 | A1 | 4/2013 | Marquette et al. |
| 2013/0187419 | A1 | 7/2013 | Worlitz et al. |
| 2015/0069811 | A1 | 3/2015 | Sachs et al. |
| 2015/0165940 | A1 | 6/2015 | Schnell et al. |
| 2016/0200228 | A1 | 7/2016 | Saren et al. |
| 2017/0043681 | A1 | 2/2017 | Seiller et al. |
| 2017/0266070 | A1 | 9/2017 | Bobey et al. |
| 2017/0283071 | A1 | 10/2017 | Velasco |
| 2018/0008507 | A1 | 1/2018 | Sarén et al. |
| 2018/0009343 | A1 | 1/2018 | Saren et al. |
| 2018/0036198 | A1 | 2/2018 | Mergl et al. |
| 2018/0098903 | A1* | 4/2018 | Vergara ................. A61F 7/0085 |
| 2018/0296389 | A1* | 10/2018 | Robst ........................ A61F 7/10 |
| 2018/0361892 | A1 | 12/2018 | Iacovone et al. |
| 2018/0361897 | A1 | 12/2018 | Lem et al. |
| 2018/0370324 | A1* | 12/2018 | Zhou .................. B60H 1/00278 |
| 2019/0143856 | A1 | 5/2019 | O'Hara et al. |
| 2020/0108752 | A1 | 4/2020 | Morishita et al. |
| 2020/0215765 | A1 | 7/2020 | Murmann et al. |
| 2020/0352778 | A1* | 11/2020 | Miller ...................... A61F 7/10 |
| 2021/0024155 | A1 | 1/2021 | Primeaux et al. |
| 2021/0115607 | A1 | 4/2021 | Inoue et al. |
| 2021/0339662 | A1 | 11/2021 | Iacovone et al. |
| 2021/0354401 | A1 | 11/2021 | Kurematsu et al. |
| 2022/0080868 | A1 | 3/2022 | Kalmutzki et al. |
| 2022/0236131 | A1 | 7/2022 | Clemente et al. |
| 2022/0274516 | A1 | 9/2022 | Withey |
| 2022/0314851 | A1 | 10/2022 | Pereny et al. |
| 2022/0314854 | A1 | 10/2022 | Pereny et al. |

FOREIGN PATENT DOCUMENTS

| | | | |
|---|---|---|---|
| CN | 113459913 | A | 10/2021 |
| CN | 112622722 | B | 3/2023 |
| DE | 10056235 | A1 | 5/2002 |
| DE | 10116696 | C1 | 9/2002 |
| DE | 10353596 | A1 | 6/2005 |
| DE | 102011122124 | A1 | 7/2012 |
| DE | 102014001678 | B3 | 7/2014 |
| DE | 102014201663 | B4 | 8/2016 |
| DE | 112017004243 | T5 | 5/2019 |
| DE | 102018101450 | A1 | 7/2019 |
| DE | 102019206830 | A1 | 11/2020 |
| DE | 102019219675 | A1 | 6/2021 |
| DE | 102017221150 | B4 | 7/2021 |
| DE | 202021103121 | U1 | 6/2022 |
| DE | 102019214576 | B4 | 5/2023 |
| EP | 2230126 | A2 | 9/2010 |
| EP | 3037703 | A1 | 6/2016 |
| EP | 2423040 | B1 | 10/2017 |
| EP | B281821 | B1 | 4/2019 |
| FR | 2692477 | A1 | 12/1993 |
| FR | 2771271 | A1 | 5/1999 |
| FR | 3036336 | B1 | 6/2017 |
| JP | 10000922 | A2 | 1/1998 |
| JP | 2000004993 | A | 1/2000 |
| JP | 2012115515 | A | 6/2012 |
| JP | 2018149799 | A | 9/2018 |
| JP | 2021074092 | A | 5/2021 |
| KR | 20140005569 | U | 10/2014 |
| KR | 101880763 | B1 | 7/2018 |
| KR | 102228215 | B1 | 3/2021 |
| WO | 2004026623 | A1 | 4/2004 |
| WO | 2015039701 | A1 | 3/2015 |
| WO | 2017025404 | A1 | 2/2017 |
| WO | 2018039472 | A1 | 3/2018 |
| WO | 2019079027 | A1 | 4/2019 |
| WO | 2020257925 | A1 | 12/2020 |
| WO | 2022051047 | A1 | 3/2022 |
| WO | 2022069934 | A1 | 4/2022 |

OTHER PUBLICATIONS https://www.tesplus.com/model-3-seat-massage-module.html, "Massage Module for Model 3/Y", 2022, 6 pages.
YouTube, "The Sterling Coilmaster Jr. TS Plastic Spiral Binding Machine", https://www.youtube.com/watch?v=8iariyFJRjY, Mar. 21, 2017, 2 pages.
International Search Report and Written Opinion for Application No. PCT/US23/25365, dated Sep. 19, 2023, 18 pages.
International Search Report and Written Opinion for Application No. PCT/US23/25473, dated Oct. 11, 2023, 11 pages.
International Search Report and Written Opinion for Application No. PCT/US2023/025395, dated Oct. 16, 2023, 20 pages.
Invitation to Pay Additional Fees for Application No. PCT/US2023/025395, dated Aug. 2, 2023, 3 pages.

(56)         References Cited

OTHER PUBLICATIONS

Invitation to Pay Additional Fees for Application No. PCT/US23/
25483, dated Aug. 14, 2023, 3 pages.
Invitation to Pay Additional Fees for Application No. PCT/US2023/
025413, dated Aug. 2, 2023, 3 pages.

* cited by examiner

HEAT TRANSFER SYSTEM FOR A THERAPY DEVICE

TECHNICAL FIELD

Various embodiments relate to heat transfer systems for therapy devices.

DETAILED DESCRIPTION

Figures 1, 2:
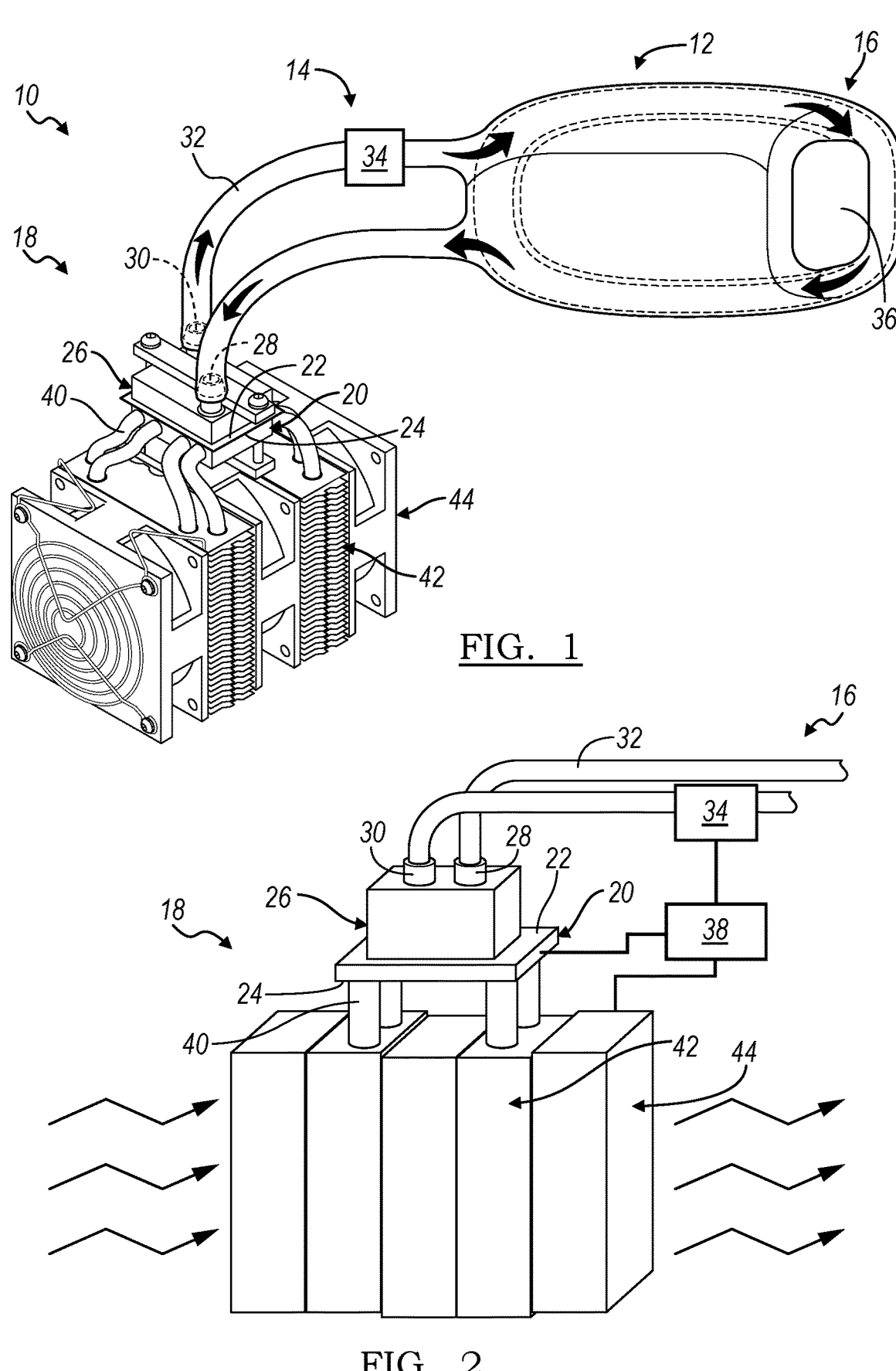
FIG. 1 illustrates a therapy device with a heat transfer system according to an embodiment.
FIG. 2 illustrates a schematic of a portion of the heat transfer system of FIG. 1.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

It is to be understood that the disclosed embodiments are merely exemplary and that various and alternative forms are possible. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ embodiments according to the disclosure.

"One or more" includes a function being performed by one element, a function being performed by more than one element, e.g., in a distributed fashion, several functions being performed by one element, several functions being performed by several elements, or any combination of the above.

It will also be understood that, although the terms first, second, etc. are, in some instances, used herein to describe various elements, these elements should not be limited by these terms. These terms are only used to distinguish one element from another. For example, a first contact could be termed a second contact, and, similarly, a second contact could be termed a first contact, without departing from the scope of the various described embodiments. The first contact and the second contact are both contacts, but they are not the same contact.

The terminology used in the description of the various described embodiments herein is for the purpose of describing particular embodiments only and is not intended to be limiting. As used in the description of the various described embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, element, components, and/or groups thereof.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIG. 1 illustrates a therapy device referenced generally by numeral 10. The therapy device 10 is depicted including a therapeutic sleeve 12. However, the therapy device 10 may include any thermal comfort device for a user, such as a thermal therapy pad, a massager, a seat assembly, or the like.

The therapy device 10 is illustrated in cooperation with a heat transfer system 14. According to an embodiment, the heat transfer system 14 is utilized to cool the therapeutic sleeve 12. The heat transfer system 14 includes two heat transfer subsystems 16, 18. The first heat transfer subsystem 16 is utilized to cool the therapeutic sleeve 12. The second heat transfer subsystem 18 is utilized to dissipate waste heat generated in order to cool the therapeutic sleeve 12.

The heat transfer system 14 includes a thermoelectric device 20. The thermoelectric device 20 is an electrical device with high electrical conductivity, a low thermal conductivity, and a temperature difference across a material of the thermoelectric device 20 in response to a thermoelectric voltage induced across the thermoelectric device 20. The material of the thermoelectric device 20 may include a conductive silicone or graphite interface for effective heat transfer.

The thermoelectric device 20 has a first heat transfer surface 22 and a second heat transfer surface 24. In the depicted arrangement, the first heat transfer surface 22 is a cooling surface 22, and consequently, the second heat transfer surface 24 is a waste heat surface 24. The first heat transfer surface 22 faces the first heat transfer subsystem 16 to transfer heat from, and thereby cool, the therapeutic sleeve 12. According to another embodiment, discussed later, the heat transfer surfaces 22, 24 may be alternated.

Figures 3, 4:
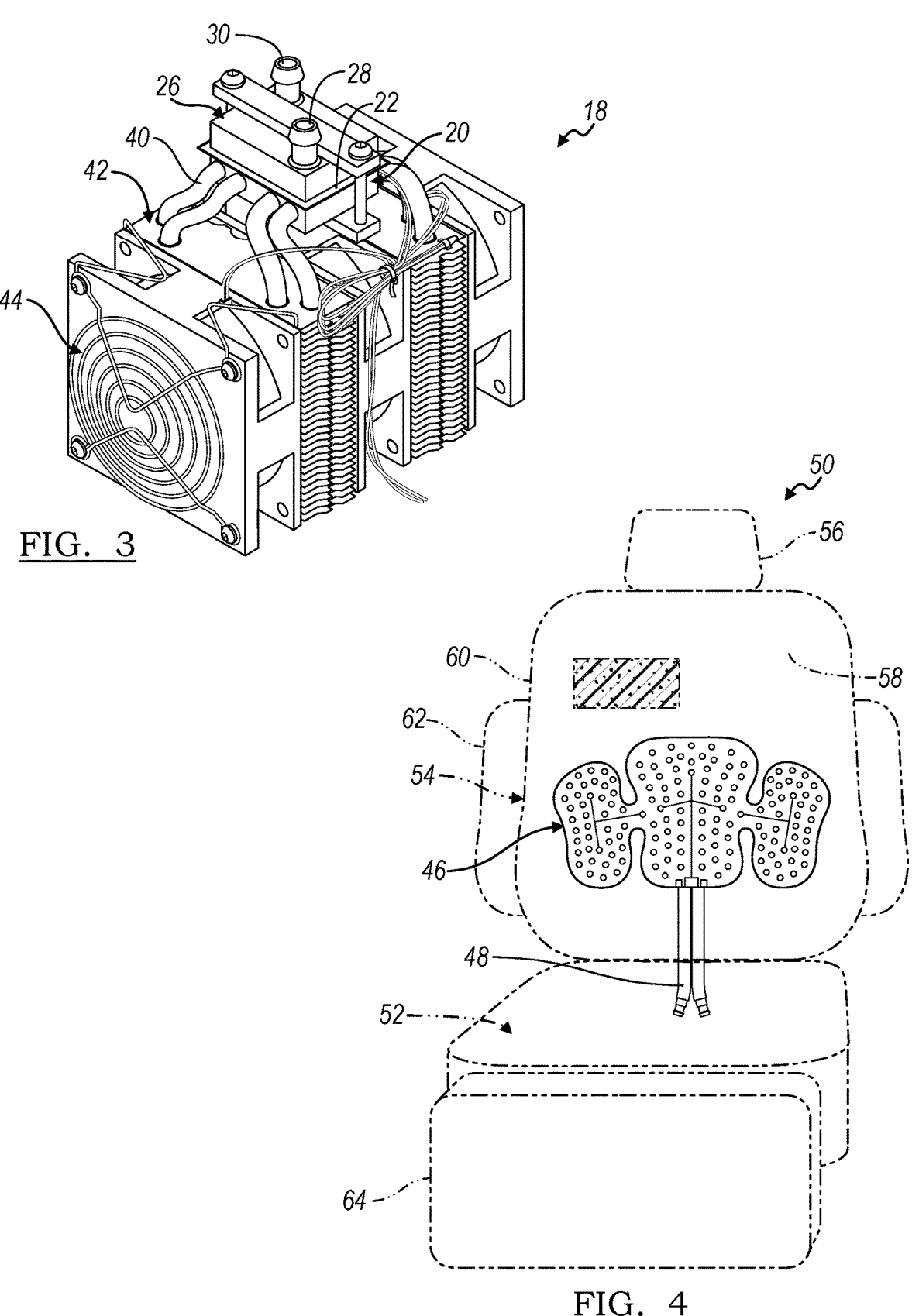
FIG. 3 illustrates a perspective view a portion of the heat transfer system of FIG. 1.
FIG. 4 illustrates a seat assembly with a heat transfer system according to another embodiment.

According to an embodiment, the heat transfer subsystem 16 is a fluid heat transfer subsystem 16. According to another embodiment, the heat transfer subsystem 16 is a liquid heat transfer subsystem 16. Referring now to FIGS. 1-3, the heat transfer subsystem 16 includes a reservoir 26 mounted directly to the first heat transfer surface 22 of the thermoelectric device 20. The reservoir 26 retains a thermally conductive fluid in the heat transfer subsystem 16. According to an embodiment, the thermally conductive fluid is water, coolant, glycol, gel, or the like. The reservoir 26 includes an inlet 28 and an outlet 30 for ingress and egress of the fluid through the reservoir 26.

As illustrated in FIGS. 1 and 2, the heat transfer subsystem 16 also includes tubing 32 in fluid communication with the inlet 28 and outlet 30 of the reservoir 26 and the therapeutic sleeve 12. A pump 34 is installed in fluid communication with the heat transfer subsystem 16, such as along the tubing 32. The pump 34 can be installed anywhere along the heat transfer subsystem 16. The tubing 32 is employed to space the therapeutic sleeve 12 away from the thermoelectric device 20, which generates a significant waste heat in order to cool the therapeutic sleeve 12. Insulation is provided on the tubing 32 to increase the efficiency of the first heat transfer subsystem 16 and to minimize absorption of ambient heat to the liquid.

The therapeutic sleeve 12 of FIG. 1 is a fluid bladder in fluid communication with the tubing 32. The therapeutic sleeve 12 includes a contact surface 36 for contact with a user. A power source 38 is depicted in FIG. 2 in electrical cooperation with the thermoelectric device 20 for cooling the fluid. The power source 38 is also in electrical cooperation with the pump 34 for pumping the fluid.

The pump 34 circulates the fluid in the first heat transfer subsystem 16 to be cooled by the first heat transfer surface 22 of the thermoelectric device 20. The cooled liquid exits the outlet 30 of the reservoir 26, travels through the tubing 32, and enters the therapeutic sleeve 12. The cooled liquid applies a cooling thermal effect to the contact surface 36, thereby absorbing heat from the user. The heated liquid is then pumped out of the therapeutic sleeve 12, through the tubing 32, and into the inlet 28 of the reservoir 26. In the reservoir 26, the liquid is then cooled by the first heat transfer surface 22, thereby continuing the cycle of cooling the therapeutic sleeve 12.

Referring now to FIGS. 1-3, the second heat transfer subsystem 18 is a conductive heat transfer subsystem 18 according to an embodiment. The second heat transfer subsystem is a fluid heat transfer subsystem 18 according to another embodiment. The second heat transfer subsystem 18 is a liquid heat transfer subsystem 18 according to yet another embodiment.

The second heat transfer subsystem 18 includes a plurality of conductive pipes 40 in conductive contact with the second heat transfer surface 24 of the thermoelectric device 20 to transfer heat to or from the second heat transfer surface 24. The thermoelectric device 20 generates significant waste heat at the second heat transfer surface 24 in order to cool the cooling surface 22. The second heat transfer subsystem 18 is employed to transfer the residual or waste heat from the second heat transfer surface 24 of the thermoelectric device 20. The conductive pipes 40 are formed from a thermally conductive material, such as copper.

The second heat transfer subsystem 18 includes a heat exchanger, such as a radiator 42, or as illustrated, a plurality of radiators 42. The conductive pipes 40 are in conductive contact with the radiators 42 to transfer heat from the second heat transfer surface 24 to the radiators 42. A fluid actuator, such as a fan 44, or a series of fans 44, are installed on the radiators 42 to convey air across the radiators 42 to transfer heat away from the radiators 42.

During operation of the second heat transfer subsystem 18, the electrical power source 38 imparts a current through the thermoelectric device 20, thereby cooling the cooling surface 22. The power source 38 also powers the fans 44 to force air over the radiators 42 to transfer heat away from the radiators 42, thereby cooling the radiators 42. The radiators 42 provide heat sinks for drawing the heat from the thermoelectric device 20.

According to another embodiment, a fluid actuator, such as a fan may be provided in fluid communication with the pipes 40 and the radiators 42 to circulate air that is heated by the second heat transfer surface 24 and cooled in the radiators 42. According to yet another embodiment, a pump may be provided in fluid communication with the pipes 40 and the radiators 42 to pump a thermally conductive liquid that is heated by the second heat transfer surface 24 and cooled in the radiators 42.

The heat transfer system 14 provides rapid and efficient thermoelectric cooling for therapy devices 10. The first heat transfer subsystem 16 pulls heat away from the therapeutic sleeve 12 to be cooled by the thermoelectric device 20 away from the therapeutic sleeve 12. The liquid heat transfer subsystem 16 provides an efficient cooling of the therapeutic sleeve 12 from the thermoelectric device 20 in comparison to conventional cooling systems.

Various modifications can be made to the heat transfer system 14 to adapt the system 14 to various specifications and applications. For example, heat transfer rates at the radiators 42 can be adjusted by adjusting the material, quantity, contact area, and size of the radiators 42. Likewise, the fans 44 can be adjusted by adjusting fan speed, size and quantity, to balance heat dissipation and acoustic output of the fan 44. The tubing 32 can be adjusted by length and insulation material to avoid cooling loss from the cooling location and the user. The pump 34 can be adapted by changing the pump speed, size, and power to alter a time of contact of the heat transfer liquid within the reservoir 26. The heat transfer liquid can also be selected or changed to vary heat transfer by thermal conductivity properties of the liquid. The reservoir 26 can also be modified by size for a particular application to affect how long or how much surface area, the liquid contacts of the thermoelectric device 20. Variations for the thermoelectric device 20 include changing power, voltage, and amperage to adjust the rate of heat transfer and cooling potential. The conductive pipes 40 can be modified by material and size to balance cost and thermally conductive properties. Additionally, the tubing 32 arrangement or configuration can be modified: for example, the tubing 32 may be wound for a cooled seat, an arm band, or the like.

Although one thermoelectric device 20 is illustrated, any quantity of thermoelectric devices 20 may be employed with the therapy device 10. Multiple, smaller thermoelectric devices 20 permit distributed cooling.

According to another embodiment, the thermoelectric device 20 may be employed for heating the first heat transfer surface 22, and consequently the therapy device 10. The heating application may be provided by reversing the orientation of, or current through, the thermoelectric device 20. In the heating application, the heat transfer liquid is heated at the thermoelectric device 20, thereby delivering heated fluid to the contact area 36 of the therapy device. Cooling is consequently performed by drawing heat through the radiators 42, and through the conductive pipes 40 to the thermoelectric device 20.

FIG. 4 illustrates a therapy device 46 according to another embodiment. The therapy device 46 is a fluid bladder 46 sized to contact a user for thermal contact therapy. The fluid bladder 46 includes tubing 48 for fluid communication with the tubing 32 of the first heat transfer subsystem 16 to receive the cooled liquid for circulation through the fluid bladder 46. The fluid bladder 46 is sized to be oriented within a seat assembly 50.

The seat assembly 50 is depicted as a vehicle seat assembly 50 for a land vehicle, aircraft, or watercraft. The vehicle seat assembly 50 may be utilized in any seating row of a vehicle. The seat assembly 50 may also be utilized as any seating assembly, such as an office chair 50 or comfort seat 50.

The seat assembly 50 includes a seat bottom assembly 52 for supporting a pelvic and thigh region of an occupant. The seat bottom assembly 52 is adapted to be supported upon an underlying support surface. According to the vehicle seat assembly 50 embodiment, the seat bottom assembly 52 is adapted to be mounted to a vehicle floor, A seatback assembly 54 extends upright from the seat bottom assembly 52 to support a back and shoulders of the occupant. A head restraint assembly 56 is supported above the seatback assembly 54.

The therapy device 46 is installed in a cushion 58 of the seatback assembly 54. The therapy device 46 is concealed by a trim cover 60 that conceals the cushion 58 and the therapy device 46. The therapy device 46 may be installed for direct contact with a concealed, internal surface of the trim cover 60. The trim cover 60 may include conductive materials, such as mesh, ribbons, conductive foams, and the like for direct, conductive heat transfer. Likewise, if the therapy device 46 is oriented partially below the cushion 58, the cushion 58 may also employ thermally conductive foam or fibers for conductive heat transfer. Therefore, the thermoelectric device 20 provides cooling without relying on convection through the seat assembly 50.

For the seat assembly 50, the second heat transfer subsystem 18 is spaced apart from the therapy device 46 to avoid discomfort, noise, and vibration at the therapy location. The second heat transfer subsystem 18 can be installed beneath the seat bottom assembly 52 or elsewhere on the vehicle, within the vehicle interior, or external of the passenger cabin.

According to another embodiment, the therapy device 46 is installed in the seat bottom assembly 52. In another embodiment, the therapy device 46 is installed in the head restraint assembly 56. In yet another embodiment, the therapy device 46 is installed in one or more armrests 62, a leg rest 64, or any contact surface within a vehicle interior.

According to a first aspect, a system is provided with a thermoelectric device with a first heat transfer surface and a second heat transfer surface adapted for cooperation with a therapy device such that the first heat transfer surface is spaced apart from a contact surface of the therapy device to transfer heat to or from the contact surface. A fluid heat transfer system is in fluid communication with the thermoelectric device to transfer heat to or from the thermoelectric device.

According to a second aspect, the system of the first aspect is provided, wherein the liquid heat transfer system is further defined as a first fluid heat transfer system in fluid communication with the first heat transfer surface to transfer heat to or from the contact surface of the therapy device.

According to a third aspect, the system of the second aspect is provided, wherein the first fluid heat transfer system is further provided with a fluid reservoir in fluid communication with the first heat transfer surface.

According to a fourth aspect, the system of the third aspect is further provided with tubing in fluid communication with the fluid reservoir and the therapy device to space the thermoelectric device away from the therapy device.

According to a fifth aspect, the system of the fourth aspect is further provided with insulation disposed about the tubing.

According to a sixth aspect, the system of the fourth aspect of the fifth aspect is further provided with a bladder in fluid communication with the tubing. The bladder further provides the contact surface.

According to a seventh aspect, the system of the sixth aspect is provided wherein the bladder is sized to be oriented within a seat assembly.

According to an eighth aspect, a seat assembly is provided with a seat bottom, a seat back, and the system of the seventh aspect.

According to a ninth aspect, the system of the sixth aspect or the seventh aspect is provided wherein the bladder is further defined as a sleeve.

According to a tenth aspect, the system of any of the third aspect to the seventh aspect, and the ninth aspect is provided wherein the first fluid heat transfer system further comprises a pump in fluid communication with the fluid reservoir to pump fluid from the fluid reservoir to the contact surface.

According to an eleventh aspect, the system of any of the second aspect to seventh aspect, the ninth aspect, and the tenth aspect is further provided with a second fluid heat transfer system in fluid communication with the second heat transfer surface to transfer heat to or from the second heat transfer surface.

According to a twelfth aspect, the system of the eleventh aspect is provided wherein the second fluid heat transfer system further comprises a heat exchanger to convey heat to or from the second heat transfer surface.

According to a thirteenth aspect, the system of the twelfth aspect is further provided with conductive pipes in conductive contact with the heat exchanger and the second heat transfer surface.

According to a fourteenth aspect, the system of the twelfth aspect or the thirteenth aspect is provided wherein the heat exchanger is further provided as a radiator.

According to a fifteenth aspect, the system of any of the twelfth aspect to the fourteenth aspect is further provided with a fluid actuator in fluid communication with the heat exchanger to convey a fluid through the heat exchanger to transfer heat to or away from the heat exchanger.

According to sixteenth aspect, the system of any of the first aspect to the seventh aspect, and the ninth aspect to the fifteenth aspect is provided wherein the thermoelectric device is further provided with a material with a high electrical conductivity, a low thermal conductivity, and a temperature difference across the material in response to an induced thermoelectric voltage across the material.

According to a seventeenth aspect, the system of the sixteenth aspect is provided, wherein the material of the thermoelectric device is further provided as a conductive silicone or graphite.

According to an eighteenth aspect, the system of any of the first aspect to the seventh aspect, and the ninth aspect to the seventeenth aspect is further provided with a power source in electrical communication with the thermoelectric device to cool the first heat transfer surface.

According to a nineteenth aspect, the system of any of the first aspect to the seventh aspect, and the ninth aspect to the eighteenth aspect is further provided with a power source in electrical communication with the thermoelectric device to heat the first heat transfer surface.

According to a twentieth aspect, the system of any of the first aspect to the seventh aspect, and the ninth aspect to the nineteenth aspect is provided wherein the liquid heat transfer system is further provided as a thermally conductive liquid.

According to a twenty-first aspect, the system of the twentieth aspect is provided wherein the thermally conductive liquid is further provided as water or coolant.

According to a twenty-second aspect, a method is provided by pumping a liquid along a front heat transfer surface of a thermoelectric device with a rear heat transfer surface. The liquid is pumped through a therapy device with a contact surface, spaced apart from the thermoelectric device.

According to a twenty-third aspect, a system is provided with a therapy device with a contact surface. A thermoelectric device is provided with a first heat transfer surface and a second heat transfer surface. A fluid reservoir is in fluid communication with the first heat transfer surface. Tubing is in fluid communication with the fluid reservoir and the therapy device to space the thermoelectric device away from the therapy device. A pump is in fluid communication with the fluid reservoir to pump fluid from the fluid reservoir to the contact surface.

While various embodiments are described above, it is not intended that these embodiments describe all possible forms according to the disclosure. In that regard, the words used in the specification are words of description rather than limitation, and it is understood that various changes may be made without departing from the spirit and scope of the disclosure. Additionally, the features of various implementing embodiments may be combined to form further embodiments according to the disclosure.

What is claimed is:

1. A system comprising: a thermoelectric device with a first heat transfer surface and a second heat transfer surface adapted for cooperation with a therapy device such that the first heat transfer surface is spaced apart from a contact surface of the therapy device to transfer heat to or from the contact surface; a fluid reservoir mounted directly to the first heat transfer surface, wherein the fluid reservoir retains the fluid; and a fluid heat transfer system in fluid communication with the thermoelectric device to transfer heat to or from the thermoelectric device.

2. The system of claim 1 wherein the fluid heat transfer system is further defined as a first fluid heat transfer system in fluid communication with the first heat transfer surface to transfer heat to or from the contact surface of the therapy device.

3. The system of claim 2 further comprising a second fluid heat transfer system in fluid communication with the second heat transfer surface to transfer heat to or from the second heat transfer surface.

4. The system of claim 3 wherein the second fluid heat transfer system further comprises a heat exchanger to convey heat to or from the second heat transfer surface.

5. The system of claim 4 further comprising conductive pipes in conductive contact with the heat exchanger and the second heat transfer surface.

6. The system of claim 1 further comprising tubing in fluid communication with the fluid reservoir and the therapy device to space the thermoelectric device away from the therapy device.

7. The system of claim 6 further comprising insulation disposed about the tubing.

8. The system of claim 6 further comprising a bladder in fluid communication with the tubing, wherein the bladder comprises the contact surface.

9. The system of claim 8 wherein the bladder is sized to be oriented within a seat assembly.

10. A seat assembly comprising:
a seat bottom;
a seat back; and
the system of claim 9.

11. The system of claim 8 wherein the bladder is further defined as a sleeve.

12. The system of claim 1 wherein the fluid heat transfer system further comprises a pump in fluid communication with the fluid reservoir to pump fluid from the fluid reservoir to the contact surface.

13. The system of claim 1 wherein the thermoelectric device further comprises a material with a high electrical conductivity, a low thermal conductivity, and a temperature difference across the material in response to an induced thermoelectric voltage across the material.

14. The system of claim 13 wherein the material of the thermoelectric device further comprises a conductive silicone or graphite.

15. The system of claim 1 further comprising a power source in electrical communication with the thermoelectric device to cool the first heat transfer surface.

16. The system of claim 1 further comprising a power source in electrical communication with the thermoelectric device to heat the first heat transfer surface.

17. The system of claim 1 wherein the fluid heat transfer system further comprises a thermally conductive liquid.

18. The system of claim 1 including:
at least one heat exchanger;
a plurality of conductive pipes having first ends in conductive contact with the second heat transfer surface and having second ends in conductive contact with the at least one heat exchanger.

19. A method comprising: mounting a reservoir directly to a first heat transfer surface of a thermoelectric device that has a second heat transfer surface opposite of the first heat transfer surface, wherein the fluid reservoir retains the fluid;
pumping the liquid along the first heat transfer surface; and
pumping the liquid through a therapy device with a contact surface, spaced apart from the thermoelectric device.

20. The method of claim 19 including conductively contacting first ends of a plurality of conductive pipes with the second heat transfer surface and conductively contacting second ends of the plurality of conductive pipes to at least one heat exchanger.

21. A system comprising:
a therapy device with a contact surface:
a thermoelectric device with a first heat transfer surface and a second heat transfer surface;
a fluid reservoir directly mounted to the first heat transfer surface, wherein the fluid reservoir retains the fluid;
tubing in fluid communication with the fluid reservoir and the therapy device to space the thermoelectric device away from the therapy device; and
a pump in fluid communication with the fluid reservoir to pump fluid from the fluid reservoir to the contact surface.

22. The system of claim 21 including:
at least one heat exchanger;
a plurality of conductive pipes having first ends in conductive contact with the second heat transfer surface and having second ends in conductive contact with the at least one heat exchanger.

* * * * *